(12) United States Patent
Hrabie et al.

(10) Patent No.: US 7,928,079 B2
(45) Date of Patent: Apr. 19, 2011

(54) POLYSACCHARIDE-DERIVED NITRIC OXIDE-RELEASING CARBON-BOUND DIAZENIUMDIOLATES

(75) Inventors: Joseph A. Hrabie, Frederick, MD (US); Larry K. Keefer, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 334 days.

(21) Appl. No.: 12/092,184

(22) PCT Filed: Oct. 16, 2006

(86) PCT No.: PCT/US2006/040456
§ 371 (c)(1),
(2), (4) Date: May 22, 2008

(87) PCT Pub. No.: WO2007/053292
PCT Pub. Date: May 10, 2007

(65) Prior Publication Data
US 2008/0306012 A1 Dec. 11, 2008

Related U.S. Application Data

(60) Provisional application No. 60/731,946, filed on Oct. 31, 2005.

(51) Int. Cl.
*A01N 43/04* (2006.01)
*A61K 31/70* (2006.01)

(52) U.S. Cl. ............... 514/35; 514/23; 514/25; 536/4.1; 536/17.2; 536/17.7; 536/123.1

(58) Field of Classification Search ................. None
See application file for complete search history.

(56) References Cited

U.S. PATENT DOCUMENTS

| | | |
|---|---|---|
| 4,954,526 A | 9/1990 | Keefer |
| 5,039,705 A | 8/1991 | Keefer et al. |
| 5,155,137 A | 10/1992 | Keefer et al. |
| 5,185,376 A | 2/1993 | Diodati et al. |
| 5,208,233 A | 5/1993 | Keefer et al. |
| 5,212,204 A | 5/1993 | Keefer et al. |
| 5,250,550 A | 10/1993 | Keefer et al. |
| 5,268,465 A | 12/1993 | Bredt et al. |
| 5,366,997 A | 11/1994 | Keefer et al. |
| 5,389,675 A | 2/1995 | Christodoulou et al. |
| 5,405,919 A | 4/1995 | Keefer et al. |
| 5,428,070 A | 6/1995 | Cooke et al. |
| 5,468,630 A | 11/1995 | Billiar et al. |
| 5,482,925 A | 1/1996 | Hutsell |
| 5,525,357 A | 6/1996 | Keefer et al. |
| 5,632,981 A | 5/1997 | Saavedra et al. |
| 5,650,447 A | 7/1997 | Keefer et al. |
| 5,658,565 A | 8/1997 | Billiar et al. |
| 5,676,963 A | 10/1997 | Keefer et al. |
| 5,683,668 A | 11/1997 | Hrabie et al. |
| 5,691,423 A | 11/1997 | Smith et al. |
| 5,700,830 A | 12/1997 | Korthuis et al. |
| 5,714,511 A | 2/1998 | Saavedra et al. |
| 5,718,892 A | 2/1998 | Keefer et al. |
| 5,721,365 A | 2/1998 | Keefer et al. |
| 5,731,305 A | 3/1998 | Keefer et al. |
| 5,814,565 A | 9/1998 | Reichert et al. |
| 5,814,666 A | 9/1998 | Green et al. |
| 5,891,459 A | 4/1999 | Cooke et al. |
| 5,910,316 A | 6/1999 | Keefer et al. |
| 5,945,452 A | 8/1999 | Cooke et al. |
| 6,096,070 A | 8/2000 | Ragheb et al. |
| 6,110,453 A | 8/2000 | Keefer et al. |
| 6,200,558 B1 | 3/2001 | Saavedra et al. |
| 6,232,336 B1 | 5/2001 | Hrabie et al. |
| 6,261,594 B1 | 7/2001 | Smith et al. |
| 6,270,779 B1 | 8/2001 | Fitzhugh et al. |
| 6,290,981 B1 | 9/2001 | Keefer et al. |
| 6,379,660 B1 | 4/2002 | Saavedra et al. |
| 6,511,991 B2 | 1/2003 | Hrabie et al. |
| 6,610,660 B1 | 8/2003 | Saavedra et al. |
| 6,673,338 B1 | 1/2004 | Arnold et al. |
| 6,703,046 B2 | 3/2004 | Fitzhugh et al. |
| 6,750,254 B2 | 6/2004 | Hrabie et al. |
| 6,911,478 B2 | 6/2005 | Hrabie et al. |
| 2004/0033242 A1 | 2/2004 | McDonald et al. |
| 2004/0092484 A1 | 5/2004 | Arnold et al. |

FOREIGN PATENT DOCUMENTS

| | | |
|---|---|---|
| EP | 1 439 187 A1 | 7/2004 |
| WO | WO 93/05773 A1 | 4/1993 |
| WO | WO 96/36326 A1 | 11/1996 |
| WO | WO 00/63462 A1 | 10/2000 |

OTHER PUBLICATIONS

Mooradian et al. Journal of Cardiovascular Pharmacology (1995), vol. 25, pp. 674-678.*
Baer et al., *Can. J. Chem.*, 51 (11), 1812-1818 (1973).
Brand et al., *Chem. Eur. J.*, 12 (2), 499-509 (2006).
Hrabie et al., *Chem. Rev.*, 102, 1135-1154 (2002).
Hrabie et al., *J. Org. Chem.*, 58, 1472-1476 (1993).

(Continued)

*Primary Examiner* — Patrick T Lewis
(74) *Attorney, Agent, or Firm* — Leydig, Voit & Mayer, Ltd.

(57) ABSTRACT

The invention relates to compounds capable of releasing nitric oxide wherein the compounds comprise a saccharide and at least one nitric oxide-releasing diazeniumdiolate [$N_2O_2$] functional group, which is bonded directly to a carbon atom of the saccharide, and methods for preparing the same. The invention further comprises the treatment of biological disorders treatable by the administration of nitric oxide.

27 Claims, 7 Drawing Sheets

OTHER PUBLICATIONS

International Search Report for PCT/US2006/040456.
Keefer et al., *Methods in Enzymology*, 28, 281-293 (1996).
Kugelman et al., *J. Chem. Soc. Perkin I*, 10, 1113-1126 (1976).
Lefer et al., *Drugs of the Future*, 19 (7), 665-672 (1994).
Saavedra et al., *Bioorg. Med. Chem. Lett.*, 10 (8), 751-753 (2000).
Schmidt et al., *Methods in Nitric Oxide Research*, 491-497 (1996).
Showalter et al., *J. Am. Chem. Soc.*, 127, 14188-14189 (2005).
Wu et al., *Tetrahedron Letters*, 42, 3779-3782 (2001).

\* cited by examiner

Figure 7

POLYSACCHARIDE-DERIVED NITRIC OXIDE-RELEASING CARBON-BOUND DIAZENIUMDIOLATES

CROSS-REFERENCE TO RELATED APPLICATIONS

This application is a national phase application under 35 U.S.C. §371 of International Application No. PCT/US2006/040456, filed on Oct. 16, 2006, which claims the benefit of U.S. Provisional Patent Application No. 60/731,946, filed on Oct. 31, 2005, all of which are specifically incorporated by reference herein in their entirety.

BACKGROUND OF THE INVENTION

Nitric oxide (NO) has been implicated as part of a cascade of interacting agents involved in a wide variety of bioregulatory processes, including the physiological control of blood pressure, macrophage-induced cytostasis and cytotoxicity, and neurotransmission (Moncada et al., "Nitric Oxide from L-Arginine: A Bioregulatory System," Excerpta Medica, International Congress Series 897, Elsevier Science Publishers B.II.: Amsterdam (1990); Marletta et al., Biofactors 2: 219-225 (1990); Ignarro, Hypertension (Dallas) 16: 477-483 (1990); Kerwin et al., J. Med. Chem. 38: 4343-4362 (1995); and Anggard, Lancet 343: 1199-1206 (1994)). Given that NO plays a role in such a wide variety of bioregulatory processes, great effort has been expended to develop compounds and devices thereof capable of releasing NO to treat biological disorders such as restenosis. Some of these compounds are capable of releasing NO spontaneously, e.g., by hydrolysis in aqueous media, whereas others are capable of releasing NO upon being metabolized (Lefer et al., Drugs Future 19: 665-672 (1994)).

Methods to regulate endogenous NO release have primarily focused on activation of enzymatic pathways with excess NO metabolic precursors like L-arginine and/or increasing the local expression of nitric oxide synthase (NOS) using gene therapy. U.S. Pat. Nos. 5,945,452, 5,891,459, and 5,428,070 describe the sustained NO elevation using orally administrated L-arginine and/or L-lysine while U.S. Pat. Nos. 5,268,465, 5,468,630, and 5,658,565 describe various gene therapy approaches. Other various gene therapy approaches have been described in the literature. See, e.g., Smith et al., "Gene Therapy for Restenosis," Curr. Cardiol. Rep., 2(1): 13-23 (2000); Alexander et al., "Gene Transfer of Endothelial Nitric Oxide Synthase but not Cu/Zn Superoxide Dismutase restores Nitric Oxide Availability in the SHRSP," Cardiovasc. Res., 47(3): 609-617 (2000); Channon et al., "Nitric Oxide Synthase in Atherosclerosis and Vascular Injury: Insights from Experimental Gene Therapy," Arterioscler. Thromb. Vasc. Biol., 20(8): 1873-1881 (2000); Tanner et al., "Nitric Oxide Modulates Expression of Cell Cycle Regulatory Proteins: A Cytostatic Strategy for Inhibition of Human Vascular Smooth Muscle Cell Proliferation," Circulation, 101(16): 1982-1989 (2000); Kibbe et al., "Nitric Oxide Synthase Gene Therapy in Vascular Pathology," Semin. Perinatol., 24(1): 51-54 (2000); Kibbe et al., "Inducible Nitric Oxide Synthase and Vascular Injury," Cardiovasc. Res., 43(3): 650-657 (1999); Kibbe et al., "Nitric Oxide Synthase Gene Transfer to the Vessel Wall," Curr. Opin. Nephrol. Hypertens., 8(1): 75-81 (1999); Vassalli et al., "Gene Therapy for Arterial Thrombosis," Cardiovasc. Res., 35(3): 459-469 (1997); and Yla-Herttuala, "Vascular Gene Transfer," Curr. Opin. Lipidol., 8(2): 72-76 (1997). In the case of preventing restenosis, however, these methods have not proved clinically effective.

Similarly, regulating endogenously expressed NO using gene therapy techniques such as NOS vectors remains highly experimental. Also, there remain significant technical hurdles and safety concerns that must be overcome before site-specific NOS gene delivery will become a viable treatment modality.

The exogenous administration of gaseous nitric oxide is not feasible due to the highly toxic, short-lived, and relatively insoluble nature of NO in physiological buffers. As a result, the clinical use of gaseous NO is largely restricted to the treatment of neonates with conditions such as persistent pulmonary hypertension (Weinberger et al., "The Toxicology of Inhaled Nitric Oxide," Toxicol. Sci., 59(1): 5-16 (2001); Kinsella et al., "Inhaled Nitric Oxide: Current and Future Uses in Neonates," Semin. Perinatol., 24(6): 387-395 (2000); and Markewitz et al., "Inhaled Nitric Oxide in Adults with the Acute Respiratory Distress Syndrome," Respir. Med., 94(11): 1023-1028 (2000)). Alternatively, however, the systemic delivery of exogenous NO with such prodrugs as nitroglycerin has long enjoyed widespread use in the medical management of angina pectoris or the "chest pain" associated with atherosclerotically narrowed coronary arteries. There are problems with the use of agents such as nitroglycerin. Because nitroglycerin requires a variety of enzymes and cofactors in order to release NO, repeated use of this agent over short intervals produces a diminishing therapeutic benefit. This phenomenon is called drug tolerance and results from the near or complete depletion of the enzymes/cofactors needed in the blood to efficiently convert nitroglycerin to a NO-releasing species. By contrast, if too much nitroglycerin is initially given to the patient, it can have devastating side effects including severe hypotension and free radical cell damage. Likewise, the use of nitrocellulose, a polymer analog of nitroglycerin, possesses potentially similar hazards as a source of NO, for example, as described in U.S. Published Patent Application 2004/0033242 A1, published Feb. 19, 2004.

One potential method for overcoming the disadvantages associated with NO prodrug administration is to provide NO-releasing therapeutics that do not require activation by endogenous enzyme systems. Early efforts to provide NO-releasing compounds suitable for in vivo use were described in U.S. Pat. No. 4,954,526.

Diazeniumdiolates comprise a diverse class of NO-releasing compounds/materials that are known to exhibit sufficient stability to be useful as therapeutics. Although discovered more than 100 years ago by Traube et al. (Liebigs Ann. Chem., 300: 81-128 (1898)), the chemistry and properties of diazeniumdiolates have been extensively reinvestigated by Keefer and co-workers, as described in U.S. Pat. Nos. 6,750,254, 6,703,046, 6,673,338, 6,610,660, 6,511,991, 6,379,660, 6,290,981, 6,270,779, 6,232,336, 6,200,558, 6,110,453, 5,910,316, 5,814,666, 5,814,565, 5,731,305, 5,721,365, 5,718,892, 5,714,511, 5,700,830, 5,691,423, 5,683,668, 5,676,963, 5,650,447, 5,632,981, 5,525,357, 5,405,919, 5,389,675, 5,366,997, 5,250,550, 5,212,204, 5,208,233, 5,185,376, 5,155,137, 5,039,705, and 4,954,526, and in Hrabie et al., J. Org. Chem., 58: 1472-1476 (1993), which are incorporated herein by reference.

Diazeniumdiolated compounds have been attached to polymers, substrates, and medical devices. See, for example, U.S. Pat. Nos. 6,703,046, 6,270,779, 6,673,338, 6,200,558, 6,110,453, 5,718,892, 5,691,423, 5,676,963, 5,650,447, 5,632,981, 5,525,357, and 5,405,919.

Keefer et al. (U.S. Pat. Nos. 4,954,526; 5,039,705; 5,155,137; 5,208,233, 5,525,357, 5,405,919, 5,718,892, 5,676,963, and 6,110,453 and related patents and patent applications, all of which are incorporated herein by reference) and Smith et al. (U.S. Pat. No. 5,691,423 which is incorporated herein by reference) disclose, among others, the use of certain nucleophile/nitric oxide adducts as NO-releasing agents, i.e., in which the nucleophile residue (Nuc) preferably is a primary amine, a secondary amine, or a polyamine. Although such adducts offer many advantages over other currently available nitric oxide-releasing compounds, one disadvantage presented by the use of such adducts as pharmaceutical agents is the potential risk of release of nitrosamines, which are carcinogenic, upon decomposition and release of NO. Another disadvantage of the adducts of primary amines is that they can be unstable even as solids due to a tendency to form traces of potentially explosive diazotates.

Furthermore, several types of compounds of the general structure are known. See Hrabie and Keefer, Chem. Rev. 102, 1135-1154 (2002) for a review of diazeniumdiolate chemistry. Traube (Liebigs Ann. Chem. 300: 81-123 (1898)) reported the preparation of a number of such compounds and noted that treatment of the compounds with acid produced a "brown gas." Although brown gas suggests the release of NO, given that a brown gas also may be produced in the disproportionation of nitrite, the release of brown gas by the compounds prepared by Traube is not, in and of itself, evidence of NO release. Compounds of the structural type reported by Traube were believed to require harsh treatment with mineral acids to release any gas.

The prior art teaches that an [$N_2O_2^-$] functional group bonded to a carbon atom through the above-described Traube reaction releases NO only after harsh treatment with mineral acids, making such compounds incompatible with biological utility. Further, Smith et al. (U.S. Pat. No. 5,691,423), for example, teaches the use of a nucleophile adduct in a two-step process to link a nitrogen-bound [$N_2O_2^-$] functional group to a carbon atom of a polysaccharide in order to obtain NO release. However, the compounds described in Smith et al. have the potential risks of releasing carcinogens upon decomposition and release of NO, and being relatively unstable. Finally, the prior art teaches another two-step process to link a nitrogen-bound [$N_2O_2^-$] functional group to a carbon atom of a polysaccharide. See Kugelman et al., J. Chem. Soc. Perkin I, 1113-1126 (1976). However, the method of Kugelman et al. results in the polysaccharide further comprising a reactive halogen atom.

Thus, despite the extensive literature available on NO and nitric oxide-releasing compounds, there remains a need for stable nitric oxide-releasing polymers, such as polysaccharides, or small molecules, such as monosaccharides and disaccharides, that exhibit a sustained release of nitric oxide and can be readily prepared during the processing of commercially available material containing monosaccharides, disaccharides, polysaccharides, or any combination thereof. Moreover, there exists a need for medicines and medical devices capable of releasing NO for an efficacious duration. Such a medicine or device is useful for treating biological disorders.

BRIEF SUMMARY OF THE INVENTION

The invention relates to polymeric or small molecule compounds capable of releasing nitric oxide wherein the compounds comprise monosaccharides, disaccharides, polysaccharides, or any combination thereof, oxygen-substituted derivatives of the described mono-, di-, and poly-saccharides, as well as other variants of mono-, di-, and poly-saccharides such as aminosugars and the like as understood by those of skill in the art, for convenience referred to as "a saccharide," and at least one diazeniumdiolate (a nitric oxide-releasing [$N_2O_2^-$] functional group), which is bonded directly to a carbon atom of the saccharide, methods of using the same, and a method for preparing the same. The nitric oxide-releasing saccharides are capable of releasing nitric oxide when the nitric oxide-releasing saccharide is exposed to pH 7.4 phosphate buffer at 37° C.

The present invention provides an advantage over the prior art in that compounds of the present invention comprise at least one [$N_2O_2^-$] functional group directly bonded to a carbon atom of a saccharide which does not require harsh treatment with mineral acids for NO release even though the compounds were prepared via a single step base-catalyzed replacement of acidic hydrogens with an NO releasing group. Further, the present invention does not require the use of a potentially hazardous nucleophile adduct to link an [$N_2O_2^-$] functional group to a carbon atom of the inventive saccharide compounds. Since the processing of raw materials, such as cotton, frequently involves treatment with a base, which increases the number of terminal saccharides in the treated cotton, the inventive method can enhance existing industrial processes by incorporating at least one [$N_2O_2^-$] functional group on to a saccharide.

The present invention further provides a method of treating biological disorders for which dosage with nitric oxide would be beneficial which comprises administering a compound comprising a saccharide, including a polymeric or small molecule compound, such as a monosaccharide, disaccharide, or polysaccharide and nitric oxide-releasing [$N_2O_2^-$] functional group bonded directly to a carbon atom of the saccharide such that the diazeniumdiolated saccharide is capable of releasing a therapeutically effective amount of nitric oxide.

BRIEF DESCRIPTION OF THE SEVERAL VIEWS OF THE DRAWING(S)

FIG. 3—(a) A short term time course NO release profile from the diazeniumdiolated regenerated cellulose membrane of Example 4; (b) A long term time course NO release profile from the diazeniumdiolated regenerated cellulose membrane of Example 4.

FIG. 6—(a) A short term time course NO release profile from the diazeniumdiolated 2,3,4,6-tetramethyl-D-glucose of Example 8; (b) A long term time course NO release profile from the diazeniumdiolated 2,3,4,6-tetramethyl-D-glucose of Example 8.

DETAILED DESCRIPTION OF THE INVENTION

The invention provides a compound capable of releasing nitric oxide comprising a monosaccharide, disaccharide, or polysaccharide, collectively referred to as "a saccharide," and at least one diazeniumdiolate (a nitric oxide-releasing $[N_2O_2^-]$ functional group) bonded directly to one or more carbon atoms of a saccharide. The $[N_2O_2^-]$ functional group is bonded directly to one or more carbon atoms of a saccharide via attachment at one of the nitrogen groups of the diazeniumdiolate [—N(O)NO]. By "bonded directly to one or more carbon atoms of a saccharide," it is meant that the $[N_2O_2^-]$ functional group does not require a nucleophilic group or other linking group bonded to the $[N_2O_2^-]$ functional group in order for the $[N_2O_2^-]$ functional group to bond to the carbon atom of a saccharide.

A saccharide is defined as a carbohydrate, and in the case of monosaccharides, a simple sugar. Monosaccharides are classified by the number of carbon atoms they contain (e.g. triose, tetrose, pentose, hexose and heptose) and by the active group, which is either an aldehyde or a ketone. Further, each carbon atom that supports a hydroxyl group (except for the first and last) is chiral, giving rise to a number of isomeric forms all with the same chemical formula. Examples of monosaccharides include, but are not limited to galactose, glucose, erythrose, threose, ribose, arabinose, xylose, lyxose, allose, altrose, mannose, gulose, idose, talose, glyceraldehyde, psicose, sorbose, tagatose, glucosamine, N-acetylglucosamine, N-acetylneuraminic acid (sialic acid), gluconolactone, inositol, sorbitol, 2,3,4,6-tetramethylglucose, and 2,3,4,6-tetrabenzylglucose. Most monosaccharides form cyclic structures, which predominate in aqueous solution, but also exist as open-chain structures. The two forms exist in equilibrium. Dissacharides are defined as two monosaccharides bonded via a condensation reaction. Polysaccharides (sometimes called glycans) are relatively complex carbohydrates made up of many monosaccharides joined together by glycosidic linkages. They are typically very large, often branched, molecules. When all the constituent monosaccharides of the polysaccharide are of the same type they are termed homopolysaccharides; when more than one type of monosaccharide is present they are termed heteropolysaccharides. The term saccharide also includes various oxygen-substituted derivatives of the described mono-, di-, and poly-saccharides, as well as other variants of mono-, di-, and poly-saccharides such as the aminosugars and the like as understood by those skilled in the art.

Physical association or bonding of an $[N_2O_2^-]$ functional group directly to one or more carbon atoms of a saccharide, provides nitric oxide-releasing saccharides which are capable of releasing nitric oxide when the nitric oxide-releasing saccharide is exposed to pH 7.4 phosphate buffer at 37° C. The nitric oxide-releasing saccharides described herein can be prepared by the base-catalyzed reaction of a nitric oxide-releasing $[N_2O_2^-]$ functional group with a saccharide, preferably, a monosaccharide, disaccharide, or polysaccharide, and more preferably, the saccharide also comprises a reducing sugar, such as glucose, which is converted to a nitric oxide-releasing diazeniumdiolate.

Applicants believe that the reaction of NO with a saccharide can be represented as follows (Equation 1):

(Eq. 1)

While not wishing to be bound by any theory, it is believed that when a saccharide is exposed to nitric oxide in the presence of a base, there are multiple reactions by which the $[N_2O_2^-]$ functional group may be forming at or bonding to the carbon atoms of saccharides potentially resulting in multiple forms of $N_2O_2^-$-modified saccharides, including, for example, open chain, modified mono-, di-, and poly-saccharides, closed ring saccharides and di- and poly-saccharides which are open and closed in the same molecule. By way of illustration only, treatment of a saccharide with a base can produce the open-chain enolate of the saccharide. The enolate-saccharide is susceptible to further tautomerization, allowing an $[N_2O_2^-]$ functional group to bond at any carbon atom of the saccharide.

Because the $[N_2O_2^-]$ functional group is bonded directly to one or more carbon atoms of a saccharide in the present inventive compounds there is no linking group or additional nucleophile such as a primary amine, a secondary amine, or a polyamine. The absence of a linking group or nitrogen-bound nucleophile adduct eliminates the potential risk of such adducts releasing potentially harmful by-products such as carcinogenic nitrosamines.

One skilled in the art will also recognize the theoretical possibility that some reactions via the open chain forms of saccharides, as detailed previously, can, in principle, be suppressed in favor of the direct reaction of the hemiacetal, or another, hydroxyl group via initial oxidation of the saccharide to the lactone following the sequence of reactions outlined by Wieland and Kerr (Ber. Dtsch. Chem. Ges., 1930, 63, 570-579) which is incorporated herein by reference (Equation 3).

(Eq. 3)

Finally, one skilled in the art will also recognize the theoretical possibility that nitric oxide may react with a saccharide via different mechanisms to produce the diazeniumdiolate-containing inventive compounds. Indeed, to some extent, the materials of the present invention may contain mixtures of the many possible molecular structures.

In particular, the present invention provides a nitric oxide-releasing saccharide, wherein at least one $[N_2O_2^-]$ functional group is directly attached to at least one carbon atom of a monosaccharide, disaccharide, or polysaccharide or even a by-product of the mono-, di-, or poly-saccharide that may result from chain opening or other reaction mechanisms that occur when a saccharide is exposed to nitric oxide in the presence of a base. The invention includes a polysaccharide comprising multiple terminal saccharides, wherein $[N_2O_2^-]$ functional groups are attached directly at least one to at least one carbon atom of the terminal saccharide. In keeping with the invention, each terminal saccharide of a polysaccharide, monosaccharide, or disaccharide can be diazeniumdiolated with numerous [$N_2O_2^-$] functional groups.

Nitric oxide detection can be determined using known techniques such as those described in U.S. Pat. Nos. 6,511,991 and 6,379,660; Keefer, et al., "NONOates(1-Substituted Diazen-1-ium-1,2 diolates) as Nitric Oxide Donors: Convenient Nitric Oxide Dosage Forms," *Methods in Enzymology*, 28: 281-293 (1996); Horstmann et al., "Release of nitric oxide from novel diazeniumdiolates monitored by laser magnetic resonance spectroscopy," *Nitric Oxide*, 6(2): 135-41 (2002); and Kitamura et al., "In vivo nitric oxide measurements using a microcoaxial electrode," *Methods Mol. Biol.*, 279: 35-44 (2004), which are incorporated herein by reference. In general, the amount of NO produced can be detected by a chemiluminescence method, electrochemical method, absorbance method, and/or the Griess assay (Schmidt et al., In Methods in Nitric Oxide Research; Feelisch, M.; Stamler, J., Eds.; "Determination of nitrite and nitrate by the Griess reaction." John Wiley and Sons, Ltd.: New York; 1996; pp. 491-497). In addition, nitric oxide assay kits are commercially available.

In another aspect, the present invention provides the inventive method of incorporating [$N_2O_2^-$] functional groups to base-catalyzed reactions to enhance existing industrial processes by bonding [$N_2O_2^-$] functional groups to saccharides found in materials, such as cotton, starches, celluloses and the like, since the processing of such materials frequently involves treatment with a base, increasing the number of terminal saccharides for diazeniumdiolates to bind. A diazeniumdiolated saccharide of the inventive compounds may be modified or derivatized. Preferably, the saccharide of the inventive compounds comprises a reducing sugar or is capable of at least partial hydrolysis to create at least one reducing sugar. Examples of saccharides comprising a reducing sugar or capable of at least partial hydrolysis to create reducing sugars include, but are not limited to, glucose, mannose, galactose, maltose, shikimic acid, lactose, ribose, erythrose, threose, xylose, cellobiose, cotton, paper, starch, cellulose, rayon, dextran, collagen, heparin, trehalose, turanose, amylase, amylopectin, xanthan, tragaganth, pullulan, pectin, guaran, gum Arabic (acacia), agar, alginate, carrageenan, chitin, chitosan, cyclodextrins, chondroitin, and hyaluronic acid. Because the reactive functionality is generated by partial hydrolysis, the starting saccharide may be wholly or partially O-alkylated (examples include methylcellulose, ethylcellulose, carboxymethylcellulose). The term saccharide is also intended to include high molecular weight glycoproteins and glycolipids, since partial hydrolysis can result in the conversion of these into suitable substrates for diazeniumdiolation.

The physical and structural characteristics of saccharides suitable for use in the present invention are not narrowly critical, but rather will depend on the end use application. It will be appreciated by those skilled in the art that where the diazeniumdiolated saccharides and diazeniumdiolated saccharides compositions of the present invention are intended for topical, dermal, percutaneous, or similar use, they need not be biodegradable. For some uses, such as ingestion or the like, it may be desirable that the diazeniumdiolated saccharides compounds dissolve in a physiological environment or that it is biodegradable.

Further, the inventive compounds and compositions can be processed into nitric oxide-releasing applications including, but not limited to, wound-healing cotton gauze, dextran blood plasma substitutes, thromboresistent dialysis membranes and filters, cellulose films and membranes, antibacterial powders, laxatives, and saccharides that target glycoproteins on antigen surfaces. These diazeniumdiolated saccharides and diazeniumdiolated compositions and devices are useful for treating biological conditions where a release of nitric oxide is beneficial.

The diazeniumdiolated saccharides and diazeniumdiolated compositions of the present invention will find utility in a wide variety of applications and in a wide variety of forms depending on the biological disorder to be treated with NO-releasing compounds. For example, the saccharide may itself be structurally sufficient to serve as an implant, patch, stent or the like. Further, by way of illustration, the diazeniumdiolated saccharides and diazeniumdiolated compositions may be incorporated into polymer matrices, substrates or the like, or it may be microencapsulated, or the like.

Site specific application of the inventive compounds and compositions enhances the selectivity of action of the nitric oxide releasing [$N_2O_2^-$] functional groups. The [$N_2O_2^-$] functional groups attached to the saccharide can be localized, so the effect of their nitric oxide release will be concentrated in the tissues with which they are in contact. If the saccharide of the inventive compounds is soluble, selectivity of action can still be arranged, for example, by attachment to or derivatization of an antibody specific to the target tissue. Similarly, attachment of an [$N_2O_2^-$] functional group bound saccharide to small peptides that mimic the recognition sequences of ligands for important receptors provides localized concentrated effect of nitric oxide release, as would attachment to oligonucleotides capable of site-specific interactions with target sequences in a nucleic acid When a saccharide is reacted with nitric oxide in the presence of a base, preferably a strong base, a diazeniumdiolated saccharide forms that is capable of releasing nitric oxide over a period of time. The release of nitric oxide can be either in vivo or ex vivo, depending on the ultimate use of the diazeniumdiolated saccharide. Preferably, the inventive compounds and compositions release nitric oxide at the intended site for treatment of a biological disorder. Accordingly, the present invention provides a method of releasing nitric oxide from a nitric oxide-releasing saccharide comprising at least one nitric oxide releasing $N_2O_2^-$ group, wherein the $N_2O_2^-$ group is attached directly to a carbon atom of the saccharide. Preferably, the release of NO is under physiological conditions. In one example, the release of NO can occur in vivo or ex vivo at about 37° C. and pH about 7, preferably 7.4. Also, preferably a diazeniumdiolated saccharide in accordance with the present invention can release NO and it preferably releases NO over a period of at least about 20 minutes, more preferably at least about 1 hour, more preferably at least about 5 hours, and most preferably at least about 1 day.

In another aspect, the invention provides for a method for preparing a dizeniumdiolated saccharide. In order to prepare a diazeniumdiolated saccharide of the present invention, a strong base is used to catalyze the reaction. In general, nitric oxide (NO) releasing materials derived, at least in part, from monosaccharides, disaccharides, polysaccharides, and combinations thereof can be prepared as follows: a solution or slurry, as appropriate, of the desired saccharide compound or a suitable derivative thereof is prepared in a solution of sodium methoxide or other strong base in methanol contained in a Parr pressure bottle. Nitrogen, argon, or other inert gas is passed through the apparatus and bubbled through the solution for a time sufficient to create an inert environment. The bottle is placed into the reactor system (see, for example, Hrabie et al., J. Org. Chem., 58, 1472 (1993)), further flushed with inert gas, and vented, and nitric oxide gas is admitted to a pressure suitable for reacting with the starting material. The reaction is stirred for a time sufficient to allow the reaction to go to completion at room temperature with the addition of NO as needed to maintain the reservoir pressure. Excess NO is then vented, and inert gas is bubbled through the resultant solution for several minutes. The product is isolated either by filtration or by concentration of the solution on a rotary evaporator, washed with solvent (e.g. methanol and/or ethyl ether), and dried in vacuo for several hours or overnight, as appropriate. These materials are stored in glass jars in a refrigerator until required for experimentation.

Any suitable base can be used; a suitable base is considered a base that can initiate the reaction without itself reacting directly with NO. Preferably, the base is a metal alkoxide of the formula MOR, wherein M is a metal cation, and R is an unsubstituted or substituted $C_{1-12}$ straight chain alkyl, or an unsubstituted or substituted $C_{3-12}$ branched chain alkyl, a phenyl, naphthyl, or $C_{1-12}$ trialkylsilyl. Preferably R is methyl, more preferably R is trimethylsilyl. Specific bases that can be used include sodium methoxide, potassium isopropoxide, sodium t-butoxide, potassium t-butoxide, lithium trimethylsilanoate, sodium trimethylsilanoate, and potassium trimethylsilanoate. Furthermore, sodium hydroxide is a suitable base for initiating the reaction. For example, sodium hydroxide can be used to initiate the reaction using either an aqueous solution or as a solution/suspension in a suitable organic solvent.

In another aspect, the invention provides a pharmaceutical composition comprising at least one novel diazeniumdiolated saccharide. Preferably, the pharmaceutical composition further comprises a pharmaceutically acceptable carrier.

One skilled in the art will appreciate that suitable methods of administering the inventive compound to a mammal, e.g., a mammal such as a human, are known, and, although more than one route can be used to administer a particular compound, a particular route can provide a more immediate and more effective reaction than another route. Pharmaceutically acceptable carriers are also well known to those who are skilled in the art. The choice of carrier will be determined, in part, both by the particular compound and by the particular method used to administer the compound. Accordingly, there are a wide variety of suitable formulations of the pharmaceutical composition of the present invention.

The inventive compound can further comprise formulations suitable for oral, inhalation, or parenteral administration Formulations suitable for oral administration can consist of (a) liquid solutions, such as an effective amount of the diazeniumdiolated saccharide dissolved in diluents, such as water or saline, (b) capsules, sachets or tablets, each containing a predetermined amount of the active ingredient, as solids or granules, (c) suspensions in an appropriate liquid, and (d) suitable emulsions.

Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. In fact, some of these normally-used compounding agents are themselves saccharides which may be converted into their nitric oxide-releasing forms for compounding with NSAIDs or other drugs to alleviate stomach irritation on consumption. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The diazeniumdiolated saccharides of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to a mammal, particularly a human, in the context of the present invention should be sufficient to effect a therapeutic response in the mammal over a reasonable time frame. The dose will be determined by the strength of the particular compounds employed (taking into consideration, at least, the rate of NO evolution, the extent of NO evolution, and the bioactivity of any decomposition products derived from the diazeniumdiolates) and the condition of the mammal (e.g., human), as well as the body weight of the mammal (e.g., human) to be treated. The size of the dose also will be determined by the existence, nature, and extent of any adverse side effects that might accompany the administration of a particular composition. A suitable dosage for internal administration is 0.01 to 100 mg/kg per day. A preferred dosage is 0.01 to 35 mg/kg per day. A more preferred dosage is 0.05 to 5 mg/kg per day. A suitable concentration in pharmaceutical compositions for topical administration is 0.05 to 15% (by weight). A preferred concentration is from 0.02 to 5%. A more preferred concentration is from 0.1 to 3%.

A nitric oxide-releasing saccharide of the present invention can be bound to a substrate. The diazeniumdiolated saccharide can be contacted with a substrate, in which, preferably, the substrate has moieties that allow for chemical bonding of the nitric oxide-releasing saccharide. See, for example, U.S. Pat. Nos. 6,703,046, 6,528,107, and 6,270,779, which are incorporated herein in their entirety.

The substrate can be of any suitable biocompatible material, such as metal, glass, ceramic, plastic, or rubber. Preferably, the substrate is metal or rubber. The substrate used in the preparation of the medical device can be derived from any suitable form of a biocompatible material, such as, for example, a sheet, a fiber, a tube, a fabric, an amorphous solid, an aggregate, dust, or the like.

Metal substrates suitable for use in the invention include, for example, stainless steel, nickel, titanium, tantalum, aluminum, copper, gold, silver, platinum, zinc, Nitinol, inconel, iridium, tungsten, silicon, magnesium, tin, alloys, coatings containing any of the above, and combinations of any of the above. Also included are such metal substrates as galvanized steel, hot dipped galvanized steel, electrogalvanized steel, annealed hot dipped galvanized steel, and the like. Preferably, the metal substrate is stainless steel.

Glass substrates suitable for use in the invention include, for example, soda lime glass, strontium glass, borosilicate glass, barium glass, glass-ceramics containing lanthanum as well as combinations thereof.

Ceramic substrates suitable for use in the invention include, for example, boron nitrides, silicon nitrides, aluminas, silicas, combinations thereof, and the like.

Plastic substrates suitable for use in the invention include, for example, acrylics, acrylonitrile-butadiene-styrene, acetals, polyphenylene oxides, polyimides, polystyrene, polypropylene, polyethylene, polytetrafluoroethylene, polyvinylidene, polyethylenimine, polyesters, polyethers, polyamide, polyorthoester, polyanhydride, polyether sulfone, polycaprolactone, polyhydroxy-butyrate valerate, polylactones, polyurethanes, polycarbonates, polyethylene terephthalate, as well as copolymers and combinations thereof. Typical rubber substrates suitable for use in the invention include, for example, silicones, fluorosilicones, nitrile rubbers, silicone rubbers, fluorosilicone rubbers, polyisoprenes, sulfur-cured rubbers, butadiene-acrylonitrile rubbers, isoprene-acrylonitrile rubbers, and the like. The substrate could also be a protein, an extracellular matrix component, collagen, fibrin or another biologic agent or a mixture thereof. Silicones, fluorosilicones, polyurethanes, polycarbonates, polylactones, and mixtures or copolymers thereof are preferred plastic or rubber substrates because of their proven bio- and hemocompatibility when in direct contact with tissue, blood, blood components, or bodily fluids.

Other suitable substrates include those described in WO 00/63462 and U.S. Pat. No. 6,096,070, and incorporated herein by reference.

In yet another aspect, the present invention can comprise medical devices which are capable of releasing nitric oxide when in use, but which are otherwise inert to nitric oxide release. Alternatively, the diazeniumdiolated saccharide, with the addition of plasticizers, lubricants, gelling agents, adhesives, or other such materials as may be required, can form the medical device itself.

A "medical device" includes any device having surfaces that contact tissue, blood, or other bodily fluids in the course of their use or operation, which are found on or are subsequently used within a mammal. Medical devices include, for example, extracorporeal devices for use in surgery, such as blood oxygenators, blood pumps, blood storage bags, blood collection tubes, blood filters including filtration media, dialysis membranes, tubing used to carry blood and the like which contact blood which is then returned to the patient or mammal. Medical devices also include endoprostheses implanted in a mammal (e.g., a human), such as vascular grafts, stents, pacemaker leads, surgical prosthetic conduits, heart valves, and the like, that are implanted in blood vessels or the heart. Medical devices also include devices for temporary intravascular use such as catheters, guide wires, amniocentesis and biopsy needles, cannulae, drainage tubes, shunts, sensors, transducers, probes and the like which are placed into the blood vessels, the heart, organs or tissues for purposes of monitoring or repair or treatment. Medical devices also include prostheses such as artificial joints such as hips or knees as well as artificial hearts. In addition, medical devices include penile implants, condoms, tampons, sanitary napkins, ocular lenses, sling materials, sutures, hemostats used in surgery, antimicrobial materials, surgical mesh, transdermal patches, and wound dressings/bandages.

Since nitric oxide has been shown to inhibit platelet aggregation (e.g., WO 93/05773), the nitric oxide-releasing polymer of the invention is useful in laboratory and medical applications and procedures that involve contact with blood. The NO-releasing polymeric material can be used in vivo, for example, to line or form blood-contacting surfaces of an in-dwelling device such as a pacemaker, an implantable pulse generator (IPG), an implantable cardiac defibrillator (ICD), a pacemaker cardioverter defibrillator (PCD), a defibrillator, a spinal stimulator, a brain stimulator, a sacral nerve stimulator, a stent, a catheter, a lead, or a chemical sensor. Examples of chemical sensors include optical or electrochemical sensors that can continuously monitor or measure physiologically important ions ($H^+$, $K^+$, $Na^+$, etc.) and gases, such as $CO_2$ and $O_2$, in the blood. Ex vivo applications include incorporation of the nitric oxide releasing polymeric material into the blood-contacting surfaces of extracorporeal sensors and circulation devices such as blood oxygenators.

For example, extracorporeal membrane oxygenation (ECMO) is a means in which blood is oxygenated outside the body. ECMO takes over the work of the lungs and is often used for newborn babies whose lungs are failing despite other treatments. The procedure involves inserting plastic tubes called cannulae into the vein and artery of the neck and/or groin. The anticoagulant heparin is given to patients on ECMO to prevent clotting in the ECMO tubing and/or the development of clots on the membrane which could break off and migrate to the lungs or brain. The most common side effect of heparin is bleeding. Accordingly, the nitric oxide-releasing saccharide compounds of the present invention have utility in combination with or as a heparin-derivative to reduce or inhibit platelet aggregation or adherence. Similar problems with clotting of membranes and filters used in dialysis procedures can be solved by constructing these materials from the compounds of the present invention.

Nitric oxide-releasing saccharide compounds of the present invention are useful for the treatment of many biological disorders. The present invention provides methods of using a nitric oxide-releasing saccharide compound of the invention. In one embodiment, a method of treating a mammal, e.g., a human, with a biological disorder treatable with nitric oxide, is provided. The method comprises administering to the mammal (e.g., human), in need thereof a diazeniumdiolated saccharide compound before exposure to nitric oxide, a composition thereof, or a saccharide-containing medical device in an amount sufficient to treat the biological disorder in the mammal (e.g., human). Preferably, the method for treating a biological disorder in a mammal in which dosage with nitric oxide is beneficial, comprises administering to a specific location on or within the mammal a medical device comprising a nitric oxide-releasing saccharide and at least one nitric oxide releasing $N_2O_2^-$ group, wherein the $N_2O_2^-$ group is attached directly to a carbon atom in the saccharide backbone, in an amount sufficient to release a therapeutically effective amount of nitric oxide. The treatment can be prophylactic or therapeutic. By "prophylactic" is meant any degree in inhibition of the onset of the biological disorder, including complete inhibition. By "therapeutic" is meant any degree in inhibition of the progression of the biological disorder in the mammal (e.g., human).

In these embodiments, "biological disorder" can be any biological disorder, so long as the disorder is treatable with nitric oxide. Suitable biological disorders include hypertension, restenosis, cancer, impotency, platelet aggregation, and a biological disorder due to a genetic defect or infection with an infectious agent, such as a virus, bacterium, fungus or parasite. Moreover, polymers of the present invention can be used to promote the growth of new blood vessels and capillaries in a process known as angiogenesis. The NO-releasing polymers of the present invention may also be used to reduce inflammation and promote healing when used as a coating or substrate for implantable medical devices.

The present invention provides a method for promoting angiogenesis in a tissue of a mammal in need thereof. The method comprises either applying or administering to the mammal a medical device comprising a nitric oxide-releasing saccharide and at least one nitric oxide releasing $N_2O_2^-$ group, wherein the $N_2O_2^-$ group is attached directly to a carbon atom in the saccharide backbone, to a specific location on or within the mammal in an amount effective to promote angiogenesis in the tissue. Conditions that can be treated in accordance with this method of the invention are characterized by insufficient vascularization (or predisposition thereto) of the affected tissue, i.e., conditions in which neovascularization is needed to achieve sufficient vascularization in the affected tissue, and include, for example, diabetic ulcers, gangrene, surgical or other wounds requiring neovascularization to facilitate healing; Buerger's syndrome; hypertension; ischemic diseases including, for example, cerebrovascular ischemia, renal ischemia, pulmonary ischemia, limb ischemia, ischemic cardiomyopathy, myocardial ischemia, ischemia of tissues such as, for example, muscle, brain, kidney and lung; and other conditions characterized by a reduction in microvasculature. Exemplary tissues in which angiogenesis can be promoted include: hypertension; ulcers (e.g., diabetic ulcers); surgical wounds; ischemic tissue, i.e., a tissue having a deficiency in blood as the result of an ischemic disease including, for example, muscle, brain, kidney and lung; ischemic diseases including, for example, cerebrovascular ischemia, renal ischemia, pulmonary ischemia, limb ischemia, ischemic cardiomyopathy, and myocardial ischemia.

The following examples further illustrate the invention but, of course, should not be construed as in any way limiting its scope.

Example 1

This example describes a generalized method of preparing nitric oxide (NO)-releasing materials derived from monosaccharides, disaccharides, or polysaccharides.

A solution or slurry (as appropriate) of the desired monosaccharide, disaccharide, or polysaccharide or a suitable derivative thereof was prepared in a solution of sodium methoxide or other strong base in methanol contained in a Parr pressure bottle. Nitrogen, argon, or other inert gas was passed through the apparatus and bubbled through the solution for 5-10 min, the bottle was placed into the reactor system (see Hrabie et al., *J. Org. Chem.*, 58, 1472 (1993)), further flushed with inert gas, and vented, and nitric oxide gas was admitted to a pressure of 5 atm. The reaction was stirred for ½-3 days at room temperature with the addition of NO as needed during the first day to maintain the reservoir pressure. Excess NO was then vented, and inert gas was bubbled through the resultant solution for 5 min. The product was isolated either by filtration or by concentration of the solution on a rotary evaporator, washed with methanol and/or ethyl ether, and dried in vacuo for several hours or overnight, as appropriate. These materials were stored in glass jars in a refrigerator until required for experimentation.

Example 2

This example describes a method of preparing a NO-releasing cotton fabric.

A solution of sodium methoxide in methanol was prepared by adding 25 mL of a commercially-obtained 25% sodium methoxide in methanol solution (Sigma-Aldrich) to 200 mL of anhydrous methanol contained in a 500 mL glass Parr hydrogenation bottle. To this was added several square pieces of 100% cotton fabric having a total weight of about 2 g, and the resulting slurry was treated with NO for 40 h as described in Example 1. The cotton pieces were removed with tongs, washed several times with methanol, squeezed dry between absorbent paper towels, and placed in a vacuum desiccator overnight for complete drying. The resulting slightly off-white pieces still weighed about 2 g, and were slightly less soft when compared to the starting fabric Example 3

This example describes another method of preparing a NO-releasing cotton fabric.

A solution of 8.0 g of commercial sodium hydroxide pellets (0.2 mole) in 200 mL distilled water was prepared in a 500 mL glass Parr hydrogenation bottle. To this was added several square pieces of 100% cotton fabric having a total weight of about 0.66 g, and the resulting slurry was treated with NO for 23 h as described in Example 1. The cotton pieces were removed with tongs, washed several times with water, squeezed dry between absorbent paper towels, and placed in a vacuum desiccator overnight for complete drying. The resulting off-white pieces still weighed about 0.66 g, and were slightly less soft when compared to the starting fabric.

Example 4

This example describes a method of preparing a NO-releasing regenerated cellulose membrane.

A solution of sodium methoxide in methanol was prepared by adding 50 mL of a commercially-obtained 25% sodium methoxide in methanol solution (Sigma-Aldrich) to 300 mL of anhydrous methanol contained in a 500 mL glass Parr hydrogenation bottle. To this was added several pieces of Spectra/Por® membrane dialysis tubing having a MW cutoff of 12-14,000 (Spectrum Medical Industries, Inc.; Houston, Tex.), and the resulting slurry was treated with NO for 72 h as described in Example 1. The pieces were allowed to settle to the bottom, the solvent was decanted, and they were rinsed three times with methanol. After drying in a vacuum desiccator overnight, the clear membrane pieces had a slight brown tinge.

Example 5

This example describes a method of preparing a NO-releasing glycogen.

A solution of sodium methoxide in methanol was (prepared by adding 5 mL of a commercially-obtained 25% sodium methoxide in methanol solution (Sigma-Aldrich) to 100 mL of anhydrous methanol contained in a 500 mL glass Parr hydrogenation bottle. To this was added 5.00 g of oyster glycogen (U.S. Biochemicals cat. no. 16445), and the resulting slurry was treated with NO for 16 h as described in Example 1. The product was isolated by filtration, washed with methanol then ethyl ether, and dried in a vacuum overnight to yield 4.77 g of off-white powder.

Example 6

This example describes a method of preparing a NO-releasing corn starch.

A solution of sodium methoxide in methanol was prepared by adding 25 mL of a commercially-obtained 25% sodium methoxide in methanol solution (Sigma-Aldrich) to 150 mL of anhydrous methanol contained in a 500 mL glass Parr hydrogenation bottle. To this was added 5.00 g corn starch, and the resulting slurry was treated with NO for 68 h as described in Example 1. The product was isolated by filtration, washed with methanol, and dried in a vacuum overnight to yield 5.00 g of off-white powder.

Example 7

This example describes a method of preparing a NO-releasing glucose derivative.

A solution of 5.00 g of glucose pentaacetate (0.0128 mole) in 100 mL of methanol was placed in a 500 mL glass Parr hydrogenation bottle. To this was added 20 mL of a commercially-obtained 25% sodium methoxide in methanol solution (Sigma-Aldrich; 0.086 mole contained NaOMe), and the cloudy solution that resulted from the almost instantaneous solvolysis of the acetate groups was treated with NO for 18 h as described in Example 1. The product precipitated as a fine powder and was isolated by filtration, washed with methanol, and dried in a vacuum overnight to yield 2.04 g of off-white solid.

Example 8

This example describes another method of preparing a NO-releasing glucose derivative.

A solution of 0.20 g of 2,3,4,6-tetramethyl-D-glucose (0.847 mmole) in 2.00 mL anhydrous THF, adding 0.114 g sodium trimethylsilanoate (1.02 mmole; 1.2 equiv.) was treated with NO for 23 h as described in Example 1. The product precipitated as a fine powder, and was isolated by filtration, washed with THF, and dried in a vacuum overnight to yield 0.165 g of light tan powder. This material exhibited a UV absorption at 254 nm with a molar extinction coefficient of about $6.0$ $mM^{-1}$ $cm^{-1}$.

Example 9

This example describes a method of preparing a NO-releasing cellobiose derivative.

A slurry of 5.00 g of α-D-cellobiose octaacetate (7.37 mmole) in 200 mL of anhydrous methanol was placed in a 500 mL glass Parr bottle. To this was added 15.2 mL of a commercially-obtained 25% sodium methoxide in methanol solution (9.0 equiv.), and the slurry stirred 15 min until a clear yellow solution had formed. This solution was treated with NO for 42 h as described in Example 1, resulting in the formation of a voluminous precipitate which was isolated by filtration, washed with methanol, and dried in a vacuum overnight to yield 2.57 g of off-white solid. This solid had UV $\lambda_{max}$=254 nm ($\epsilon$=5.2 $mM^{-1}$ $cm^{-1}$).

Example 10

This example describes a generalized method of detecting nitric oxide (NO)-release from NO-releasing materials derived from monosaccharides, disaccharides or polysaccharides.

The diazeniumdiolated saccharide was slurried in pH 7.4 phosphate buffer at 37° C. and the release of NO monitored by detection of the chemiluminescence generated by treatment of the effluent gas stream with ozone.

Example 11

This example describes a method of detecting NO-release from the diazeniumdiolated cotton of Example 2.

Figure 1:
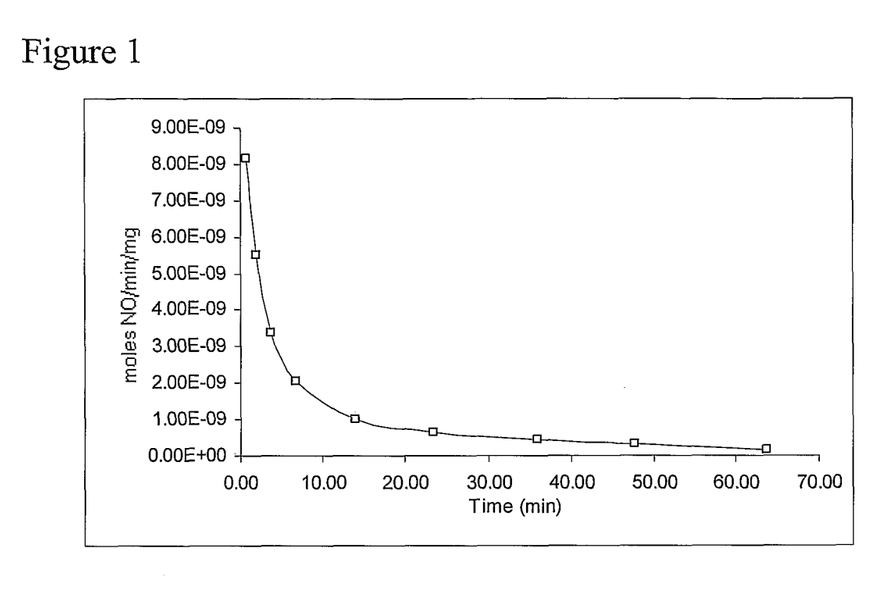
FIG. 1—The time course NO release profile from the diazeniumdiolated cotton of Example 2.

The diazeniumdiolated cotton fabric of Example 2 was slurried in pH 7.4 phosphate buffer at 37° C. and the release of NO monitored by detection of the chemiluminescence generated by treatment of the effluent gas stream with ozone.

Example 12

This example describes a method of detecting NO-release from the diazeniumdiolated cotton of Example 3.

Figure 2:
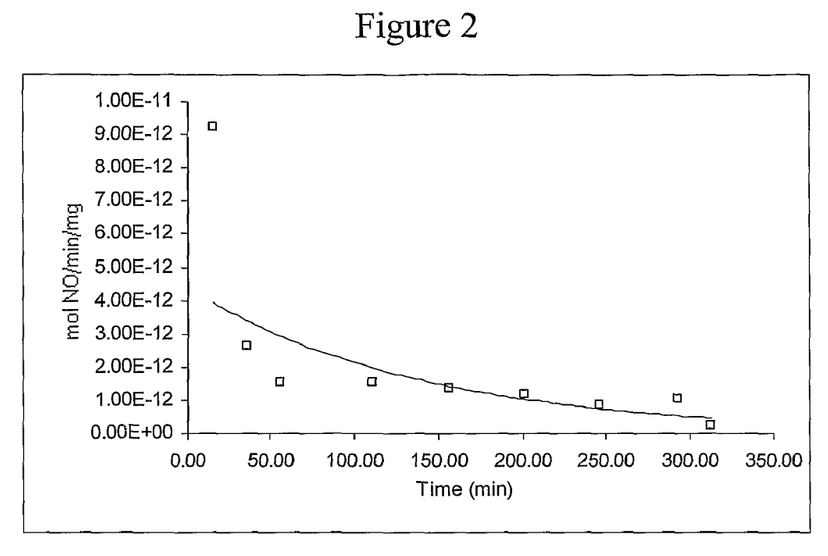
FIG. 2—The time course NO release profile from the diazeniumdiolated cotton fabric of Example 3.

The diazeniumdiolated cotton fabric of Example 3 was slurried in pH 7.4 phosphate buffer at 37° C. and the release of NO monitored by detection of the chemiluminescence generated by treatment of the effluent gas stream with ozone.

Example 13

This example describes a method of detecting NO-release from the diazeniumdiolated regenerated cellulose membrane of Example 4.

Figure 3A:
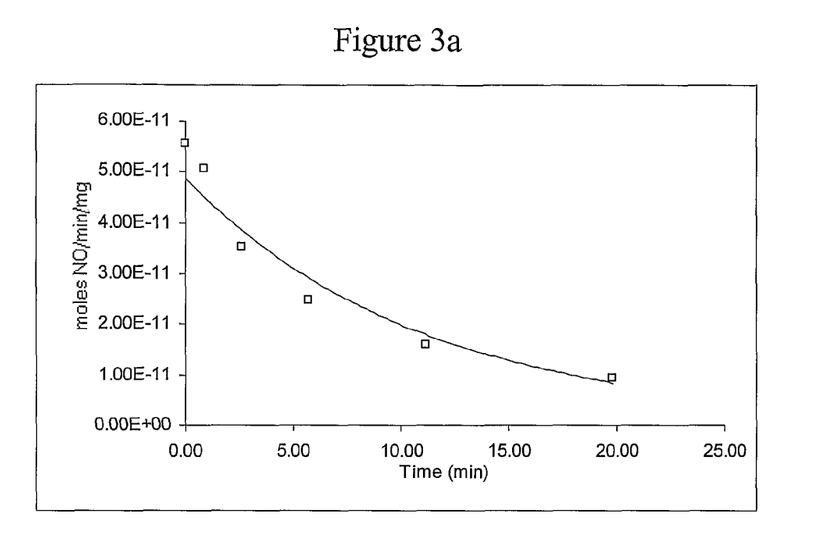
Figure 3B:
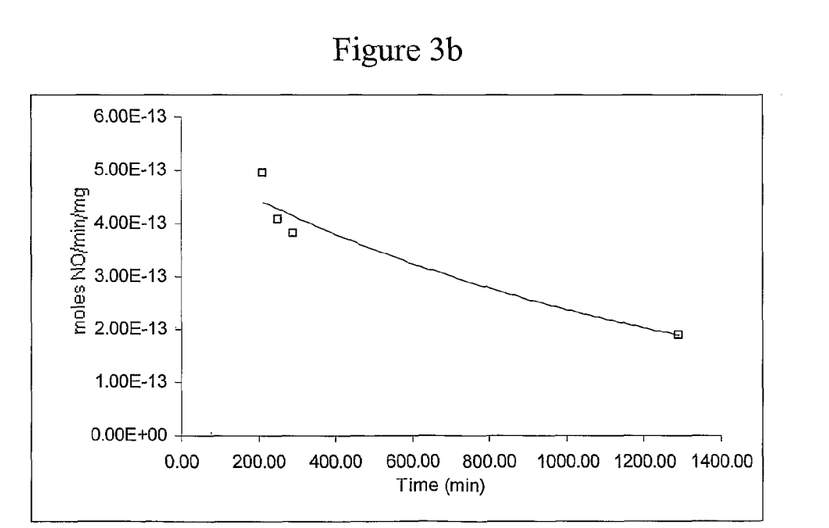

The diazeniumdiolated regenerated cellulose membrane of Example 4 was slurried in pH 7.4 phosphate buffer at 37° C. and the release of NO monitored by detection of the chemiluminescence generated by treatment of the effluent gas stream with ozone.

Example 14

This example describes a method of detecting NO-release from the diazeniumdiolated glycogen of Example 5 regenerated.

Figure 4:
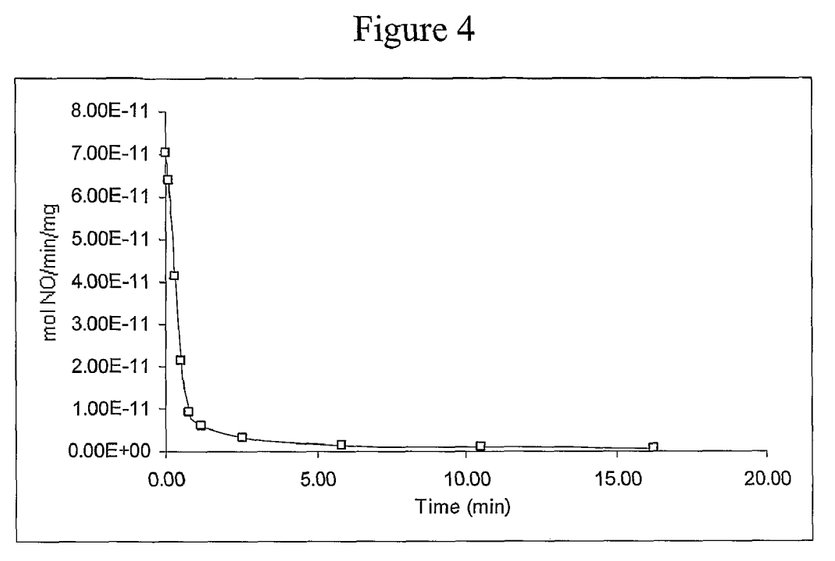
FIG. 4—The time course NO release profile from the diazeniumdiolated glycogen of Example 5.

The diazeniumdiolated glycogen of Example 5 was slurried in pH 7.4 phosphate buffer at 37° C. and the release of NO monitored by detection of the chemiluminescence generated by treatment of the effluent gas stream with ozone.

Example 15

This example describes a method of detecting NO-release from the diazeniumdiolated corn starch of Example 6.

Figure 5:
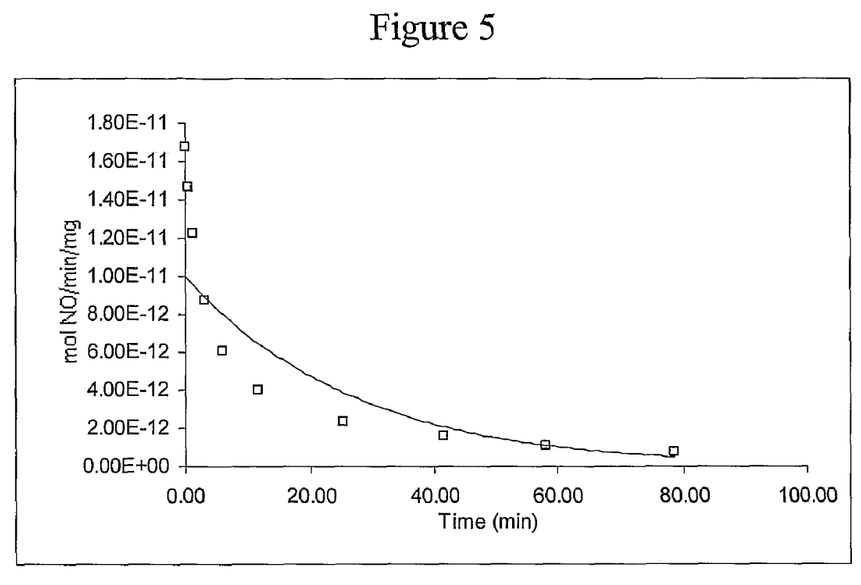
FIG. 5—The time course NO release profile from the diazeniumdiolated corn starch of Example 6.

The diazeniumdiolated corn starch of Example 6 was slurried in pH 7.4 phosphate buffer at 37° C. and the release of NO monitored by detection of the chemiluminescence generated by treatment of the effluent gas stream with ozone.

Example 16

This example describes a method of detecting NO-release from the diazeniumdiolated 2,3,4,6-tetramethyl-D-glucose of Example 8.

Figure 6A:
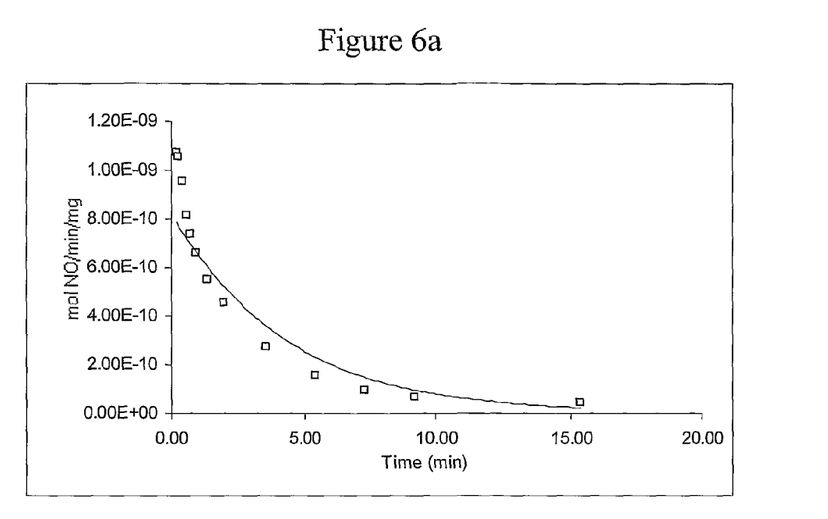
Figure 6B:
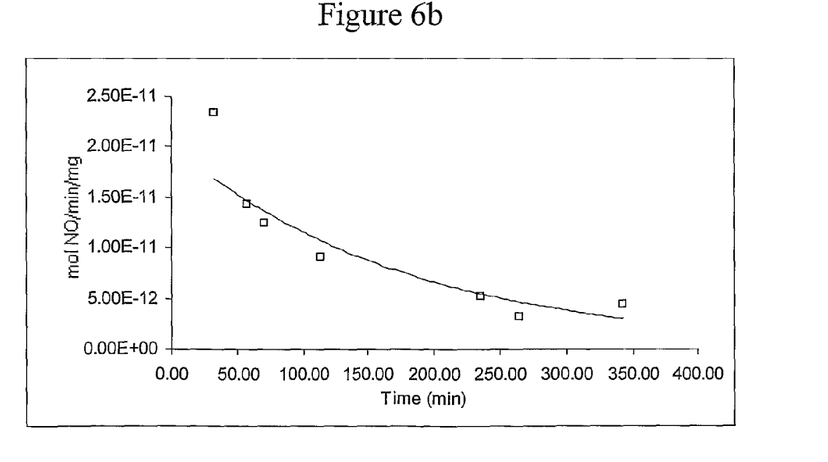

The diazeniumdiolated 2,3,4,6-tetramethyl-D-glucose of Example 8 was slurried in pH 7.4 phosphate buffer at 37° C. and the release of NO monitored by detection of the chemiluminescence generated by treatment of the effluent gas stream with ozone.

Example 17

This example describes a method of detecting NO-release from the diazeniumdiolated cellobiose of Example 9.

Figure 7:
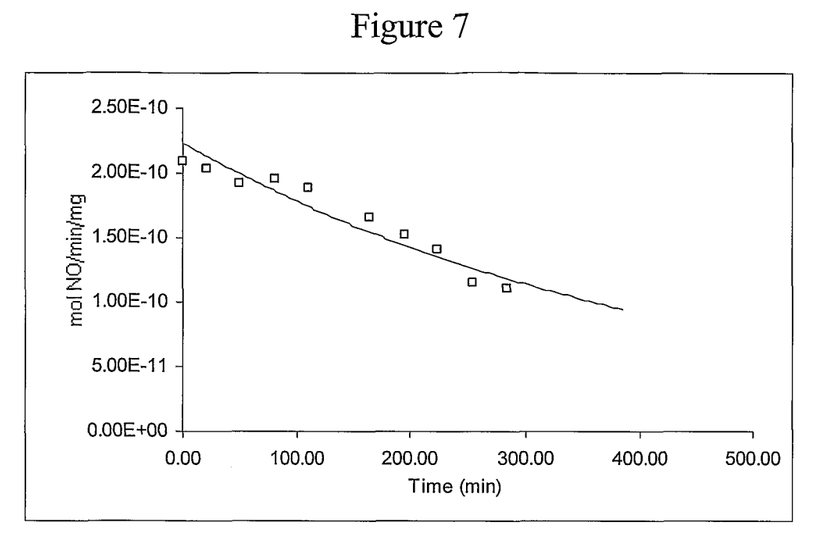
FIG. 7—The time course NO release profile from the diazeniumdiolated cellobiose of Example 9.

The diazeniumdiolated cellobiose of Example 9 was slurried in pH 7.4 phosphate buffer at 37° C. and the release of NO monitored by detection of the chemiluminescence generated by treatment of the effluent gas stream with ozone.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A nitric oxide-releasing saccharide comprising a saccharide and having an [$N_2O_2^-$] functional group bonded directly to at least one carbon atom of the saccharide via attachment at one of the nitrogens of the [$N_2O_2^-$] functional group, wherein said nitric oxide-releasing saccharide includes a first carbon (i) ketone or aldehyde, (ii) hydroxyl, or (iii) glycosidic linkage and is capable of releasing nitric oxide when said nitric oxide-releasing saccharide is exposed to pH 7.4 phosphate buffer at 37° C.

2. The nitric oxide-releasing saccharide of claim 1, wherein said saccharide is a monosaccharide.

3. The nitric oxide-releasing saccharide of claim 1, wherein said saccharide is a disaccharide.

4. The nitric oxide-releasing saccharide of claim 1, wherein said saccharide is a polysaccharide.

5. The nitric oxide-releasing saccharide of claim 4, wherein said polysaccharide is cotton.

6. The nitric oxide-releasing saccharide of claim 4, wherein said polysaccharide is paper.

7. The nitric oxide-releasing saccharide of claim 4, wherein said polysaccharide is starch.

8. The nitric oxide-releasing saccharide of claim 4, wherein said polysaccharide is cellulose.

9. The nitric oxide-releasing saccharide of claim 4, wherein said polysaccharide is heparin.

10. The nitric oxide-releasing saccharide of claim 4, wherein said polysaccharide is dextran.

11. The nitric oxide-releasing saccharide of claim 2, wherein said monosaccharide is glucose.

12. A nitric oxide-releasing saccharide formed by subjecting a saccharide to nitric oxide in the presence of a base.

13. The nitric oxide-releasing saccharide of claim 12, wherein said saccharide is a monosaccharide.

14. The nitric oxide-releasing saccharide of claim 12, wherein said saccharide is a disaccharide.

15. The nitric oxide-releasing saccharide of claim 12, wherein said saccharide is a polysaccharide.

16. The nitric oxide-releasing saccharide of claim 15, wherein said polysaccharide is cotton.

17. The nitric oxide-releasing saccharide of claim 15, wherein said polysaccharide is paper.

18. The nitric oxide-releasing saccharide of claim 15, wherein said polysaccharide is starch.

19. The nitric oxide-releasing saccharide of claim 15, wherein said polysaccharide is cellulose.

20. The nitric oxide-releasing saccharide of claim 15, wherein said polysaccharide is heparin.

21. The nitric oxide-releasing saccharide of claim 15, wherein said polysaccharide is dextran.

22. The nitric oxide-releasing saccharide of claim 13, wherein said monosaccharide is glucose.

23. A method of treating a biological disorder treatable with nitric oxide, which method comprises administering a nitric oxide-releasing saccharide of claim 1 in an amount sufficient to treat the biological disorder.

24. The method of claim 23, wherein the biological disorder is restenosis.

25. A method of treating a biological disorder treatable with nitric oxide, which method comprises administering a nitric oxide-releasing saccharide of claim 12 in an amount sufficient to treat the biological disorder.

26. The method of claim 25, wherein the biological disorder is restenosis.

27. The method of claim 25, wherein the biological disorder is selected from the group consisting of hypertension, cancer, impotency, platelet aggregation, infection by virus, bacterium, fungus or parasite, diabetic ulcer, Buerger's syndrome, and ischemia.

* * * * *